United States Patent [19]

Putman

[11] Patent Number: 5,441,042

[45] Date of Patent: * Aug. 15, 1995

[54] ENDOSCOPE INSTRUMENT HOLDER

[76] Inventor: John M. Putman, 3707 Gaston Ave., Suite 410, Dallas, Tex. 75246

[*] Notice: The portion of the term of this patent subsequent to Feb. 9, 2010 has been disclaimed.

[21] Appl. No.: 171,923

[22] Filed: Dec. 22, 1993

Related U.S. Application Data

[63] Continuation-in-part of Ser. No. 15,393, Feb. 8, 1993, Pat. No. 5,351,676, which is a continuation-in-part of Ser. No. 740,413, Aug. 5, 1991, Pat. No. 5,184,601.

[51] Int. Cl.⁶ .............................................. A61B 1/00
[52] U.S. Cl. ...................................... 601/109; 601/114
[58] Field of Search ............... 248/316.5; 128/4, 6, 128/20; 606/130, 170, 46, 208; 604/180

[56] References Cited

U.S. PATENT DOCUMENTS

| | | | |
|---|---|---|---|
| 3,043,448 | 7/1962 | Melton | 901/17 X |
| 3,575,301 | 4/1971 | Panissidi | 901/16 X |
| 4,229,136 | 10/1980 | Panissidi | 901/16 X |
| 4,510,926 | 4/1985 | Inaba | 128/20 |
| 4,572,594 | 2/1986 | Schwartz . | |
| 4,573,452 | 3/1986 | Greenberg | 128/20 |
| 4,593,681 | 6/1986 | Soni | 128/4 |
| 4,601,284 | 7/1986 | Arakawa et al. | 128/6 |
| 4,607,897 | 8/1986 | Schwartz . | |
| 4,854,301 | 8/1989 | Nakajima | 128/4 |
| 4,867,404 | 9/1989 | Harrington et al. | 248/231.4 |
| 5,061,018 | 10/1991 | Pederson . | |
| 5,224,680 | 6/1993 | Greenstein et al. | 128/20 X |

FOREIGN PATENT DOCUMENTS

| | | |
|---|---|---|
| 0239409 | 9/1987 | European Pat. Off. . |
| 0326768A3 | 8/1989 | European Pat. Off. . |
| 0456103A2 | 11/1991 | European Pat. Off. . |
| 0456103A3 | 11/1991 | European Pat. Off. . |
| 2232655A | 12/1990 | United Kingdom . |
| 1268278 | of 0000 | U.S.S.R. . |

OTHER PUBLICATIONS

Brochure, "Elmed Endoscopic Fixation Device", Elmed Incorporated (not dated).

Primary Examiner—Richard J. Apley
Assistant Examiner—Beverly A. Meindl
Attorney, Agent, or Firm—Dennis T. Griggs

[57] ABSTRACT

A portable console includes a universal positioning arm employing a clamp having quick disconnect means for releasably holding a surgical instrument such as an endoscope during a surgical procedure. The clamp includes a shaft with a bayonet connector disposed thereon, for lockably engaging a collar attached to the positioning arm. The bayonet connector includes flared spring arms which compress and engage the collar for releasably coupling the clamp to the collar.

16 Claims, 7 Drawing Sheets

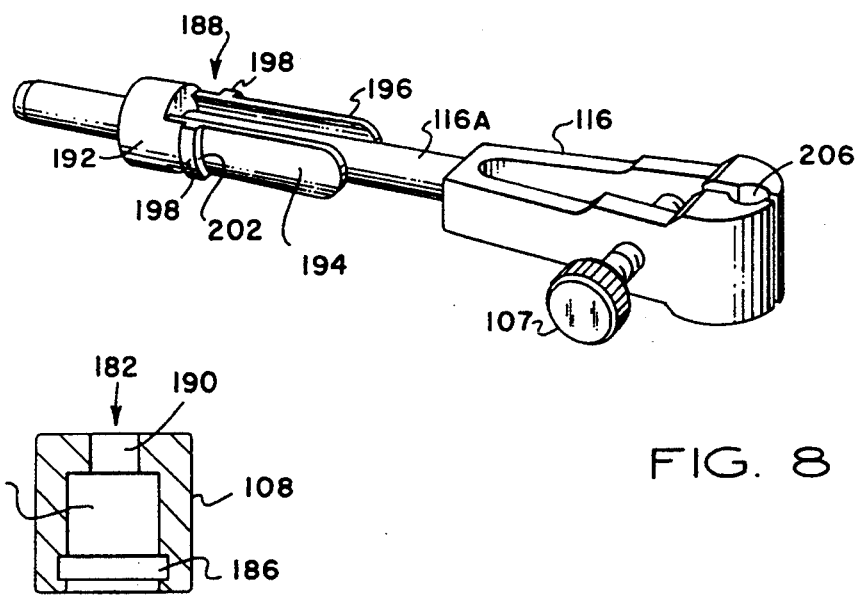
FIG. 8
FIG. 9
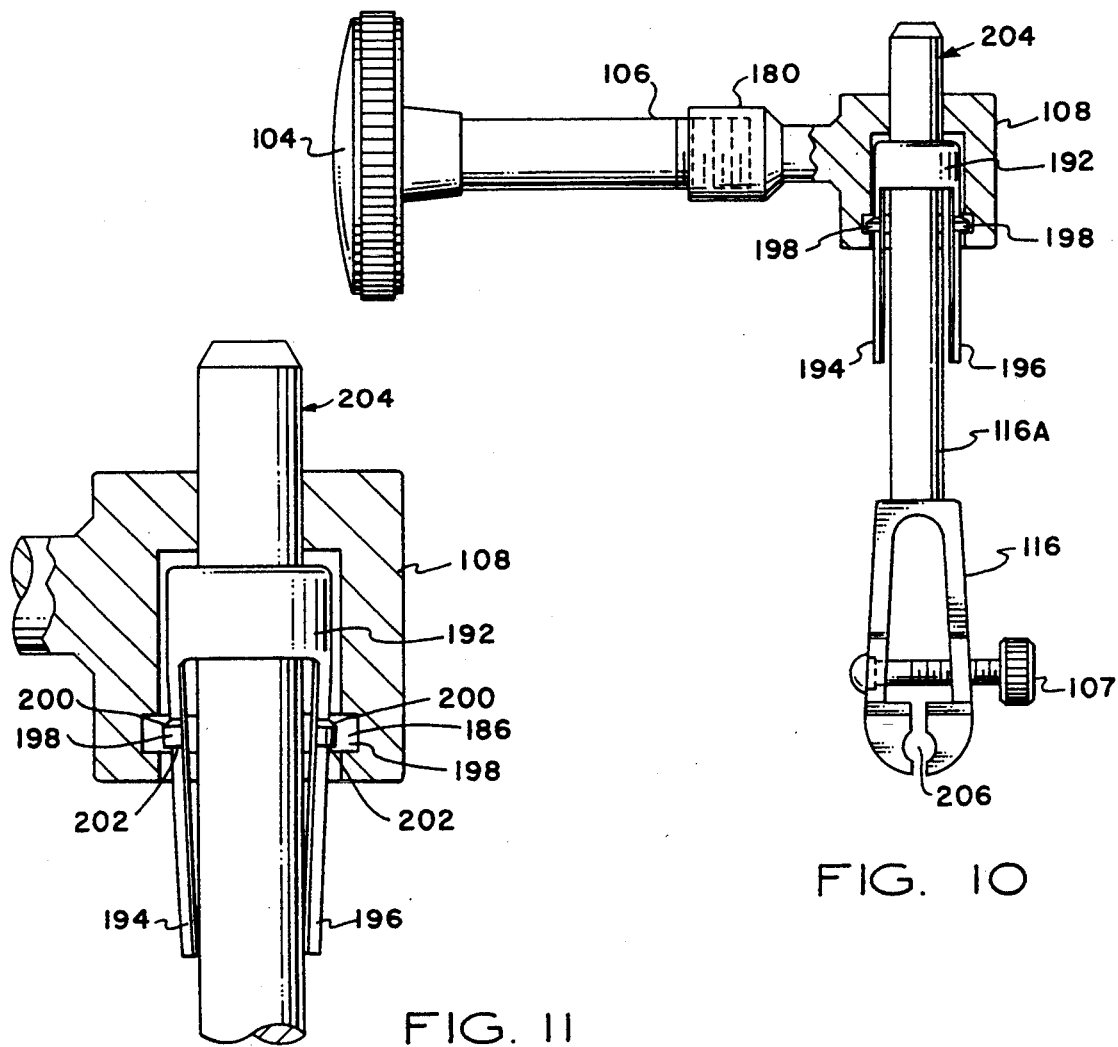
FIG. 10
FIG. 11

ENDOSCOPE INSTRUMENT HOLDER

CROSS-REFERENCE TO RELATED APPLICATIONS

This application is a continuation-in-part of application Ser. No. 08/015,393 filed Feb. 8, 1993, now U.S. Pat. No. 5,351,676 which is a continuation of application Ser. No. 07/740,413 filed Aug. 5, 1991, now U.S. Pat. No. 5,184,601.

FIELD OF THE INVENTION

This invention relates generally to the art of universal positioning devices, and in particular to a manually releasable clamp assembly for holding an instrument such as an endoscope during a surgical procedure.

BACKGROUND OF THE INVENTION

In the performance of surgery and related procedures, sterile operating conditions are maintained by a surgical drape which covers the patient and the operating table. The surgical procedure is performed through a slit or preformed fenestration which is aligned with a desired surgical site. It is sometimes necessary to support and stabilize an instrument such as an endoscope in an elevated position above the patient for long periods of time, with a portion of the instrument being inserted into the patient's abdominal cavity. The purpose of the endoscope instrument is to provide visual access into a body cavity, for example, the abdominal cavity, the knee, shoulder, bladder, uterus and bowel. A laparoscope is a type of endoscope which includes a rigid viewing tube for insertion through the abdominal wall.

It is necessary to vary the position of the instrument from time to time according to the needs of the surgical procedure. During a laparoscopic cholecystectomy (gall bladder removal), for example, an endoscope is inserted into the upper abdominal cavity which is inflated and pressurized with carbon dioxide by an insufflating machine. The endoscope is guided through a trocar sheath which serves as an interface port through the abdominal wall. By sliding the endoscope up and down the port, or rotating it in the desired direction, a view of the internal organs can be obtained by a video camera which is attached to the endoscope, and with the image being displayed on a video monitor.

The video camera also records the movement of other surgical instruments, for example, a grasper, a hook, a spatula, forceps and dissector, which are guided into and out of the abdominal cavity through one or more secondary surgical trocar sheaths. When the distal tip of the instrument appears on the video monitor, the surgeon guides it into place and controls its action and movement as displayed on the video monitor. It is usually necessary to re-position the endoscope from time to time to view the operative site so that the surgical instruments are positioned appropriately within the cavity to expose the organ or internal tissue for inspection, repair, dissection or excision.

The success of the laparoscopy procedure depends in part on the surgeon's ability and to gauge spatial relationships as viewed on the video monitor, and to be able to easily adjust or reposition the endoscope as the procedure progresses. During gall bladder removal, for example, it may be necessary to reposition the endoscope and hold it in a desired orientation as the gall bladder duct is sealed by a surgical clip. Additionally, it may be necessary to re-position the endoscope while using an electrocautery instrument to excise the gall bladder from the underside of the liver. After the gall bladder organ has been severed, it is removed through an exit port. It is then necessary to re-position the endoscope to an upper midline port so that the surgeon can correctly position and operate a grasper instrument through a secondary trocar port.

Examples of procedures which may be performed or assisted by endoscopy include the following:

| | | |
|---|---|---|
| Diagnostic | Tubal Sterilization | Ablation Endometriosis |
| Ovarian Biopsy | Ovarian Cys Aspiration | Ovarian Cystectomy |
| Ovarian Endocoagulation | Oophorectomy | Laster Uterine Nerve Ablation |
| Presacral Neurectomy | Salpingoplasty | Salpingostomy |
| Salpingectomy | Tubal Reanastomosis | Myomectomy |
| Pelvic Abscess | Removal of foreign body (IUD) | In Vitro Fertilization |
| Hysterectomy | Ovarian Torsion | Multiple Peritoneal Biopsies |
| Omentectomy | Lymphadenectomy | Lysis Bowel Adhesions |
| Appendectomy | Cholecystectomy | Colectomy |
| Hernia Repair | Gonadectomy | Nephrectomy |

Other procedures which may be assisted by endoscopy include orthopedic knee surgery, orthopedic shoulder surgery, urological procedures, bowel procedures, and other gynecological procedures.

DESCRIPTION OF THE PRIOR ART

In the performance of surgical procedures within the abdominal cavity in which an endoscope instrument is utilized, the endoscope instrument is inserted into the abdominal cavity and must be supported and held in a fixed position during the procedure, and its position must be adjusted from time to time. Once the precise anatomy-viewing position is established, it must be securely maintained. Otherwise, the physician's view will be interrupted, prolonging the procedure, with loss of visual contact at a critical moment during the operation. Moreover, the laparoscope instrument might, due to slippage, exert pressure on tissues and soft organs, such as the liver, pancreas and intestines.

In some cases, operating room personnel manually hold the endoscope instrument in the desired position, and move it about according to the surgeon's instructions. The use of operating room personnel to support such instruments during an extended surgical procedure is unsatisfactory in that the assistant may be unable to maintain stability because of muscle fatigue, and find it necessary to change position at some critical or otherwise inconvenient time.

Support devices which are mountable onto an operating table have been used for holding surgical instruments such as endoscopes and retractors. Such equipment may be clamped onto the operating table and are moved about from time to time as required by the surgical procedure. However, such devices may restrict access to the surgical site and have limited maneuverability.

Operating tables are provided with narrow side rails on which surgical support equipment may be attached. However, because the side rails are closely located to the sterile operating field, certain instrument support positions are difficult to achieve with such rail-mounted support apparatus. Generally, it is desirable to support surgical instruments in offset relation with respect to the operating table and side rails to allow a wide range of support positions.

Moreover, some rail-mounted positioning equipment must be manually released from time to time to re-position instruments which are suspended above the sterile operating zone. It will be appreciated that in surgical procedures, time is of the essence, and delays associated with adjustment of support equipment prolong the procedure. Additionally, the presence of surgical support equipment within the sterile operating zone limits the surgeon's access to the patient during the procedure. Thus, it is generally desirable to limit the number of surgical support devices in and about the sterile zone so that the operating surgeon and his attendants will have clear and unrestricted access to the patient, and also will have a clear and unrestricted view of a video monitor.

During certain procedures, it may be desirable to impose or change a biasing force on the surgical instrument to stabilize its position within the abdominal cavity. It is awkward or impossible in some instances to apply such bias forces through instruments or apparatus which are mounted directly on the side rail. Thus, it is desirable to offset such equipment both laterally and vertically in the regions immediately surrounding the sterile zone of the operating table.

Accordingly, there is a specific need for surgical instrument support apparatus which may be set up on a portable console outside of the sterile field for supporting a surgical instrument, such as an endoscope, at a desired viewing position and orientation within a body cavity, with the position of the instrument supporting apparatus being stable when set, being easily and quickly adjustable to other support positions as desired, and including a quick-disconnect clamp for easily removing the instrument without disturbing the sterile environment.

SUMMARY OF THE INVENTION

To overcome the limitations in the prior art described above, and to overcome other limitations that will become apparent upon reading and understanding the present specification, the present invention discloses a portable console having a universal positioning arm employing a quick-disconnect clamp, for holding and stabilizing a surgical instrument such as an endoscope during a surgical procedure, which is quickly and easily adjustable over a wide range of stable support positions. The quick-disconnect clamp is easily engaged and disengaged with a portion of the positioning arm forming a receptive cavity. The positioning arm is shielded by a sterile drape and the clamp is engageable and disengageable thereto without contamination. The quick-disconnect clamp is made of a disposable material or a material suitable for resterilization. The clamp may be quickly and easily removed without disturbing the placement of the positioning arm or the sterile environment.

ADVANTAGES OF THE INVENTION

An advantage of the present invention is providing a portable console having an articulated arm which can be extended and moved about within the sterile zone overlying an operating table and including a quickly releasable clamp for holding the instrument which may be disposed of or resterilized.

Another advantage of the present invention is that the quick disconnect clamp can be engaged or disengaged without removal of the drape used to maintain the sterile environment.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a specific example of a support apparatus employing a quick disconnect endoscope instrument holder, practiced in accordance with the principles of the present invention.

BRIEF DESCRIPTION OF THE DRAWINGS

Referring now to the drawings in which like reference numerals and letters indicate corresponding elements throughout the several views:

FIG. 8 is a perspective side view of the quick-disconnect clamp depicted in FIG. 6;

FIG. 9 is a cross-sectional view taken approximately along the line 9—9 in FIG. 7;

FIG. 10 is a partially cut away view of the collar and quick disconnect clamp depicted in FIG. 6;

FIG. 11 is an enlarged cut away view depicting the quick disconnect clamp engaged in the collar.

DETAILED DESCRIPTION OF THE PREFERRED EMBODIMENT

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

The surgical instrument support apparatus 10 of the present invention is particularly well suited for use in combination with a conventional surgical operating table 12 during the performance of abdominal, pelvic, joint, bladder, bowel and uterine surgery.

Figure 1:
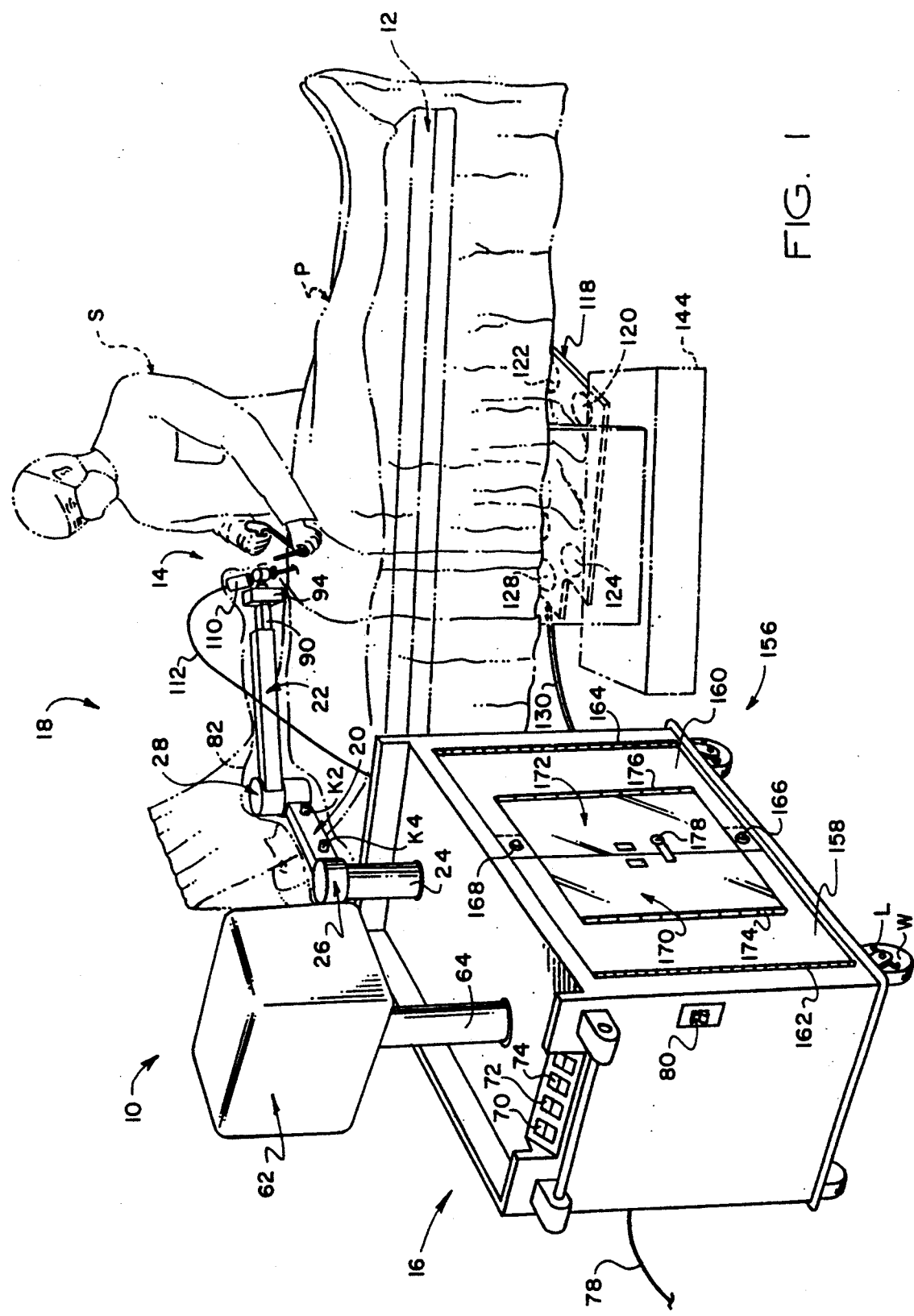
FIG. 1 is a perspective view of a portable console positioning apparatus practiced in accordance with the principles of the present invention shown set up adjacent to a surgical operating table.
Figure 2:
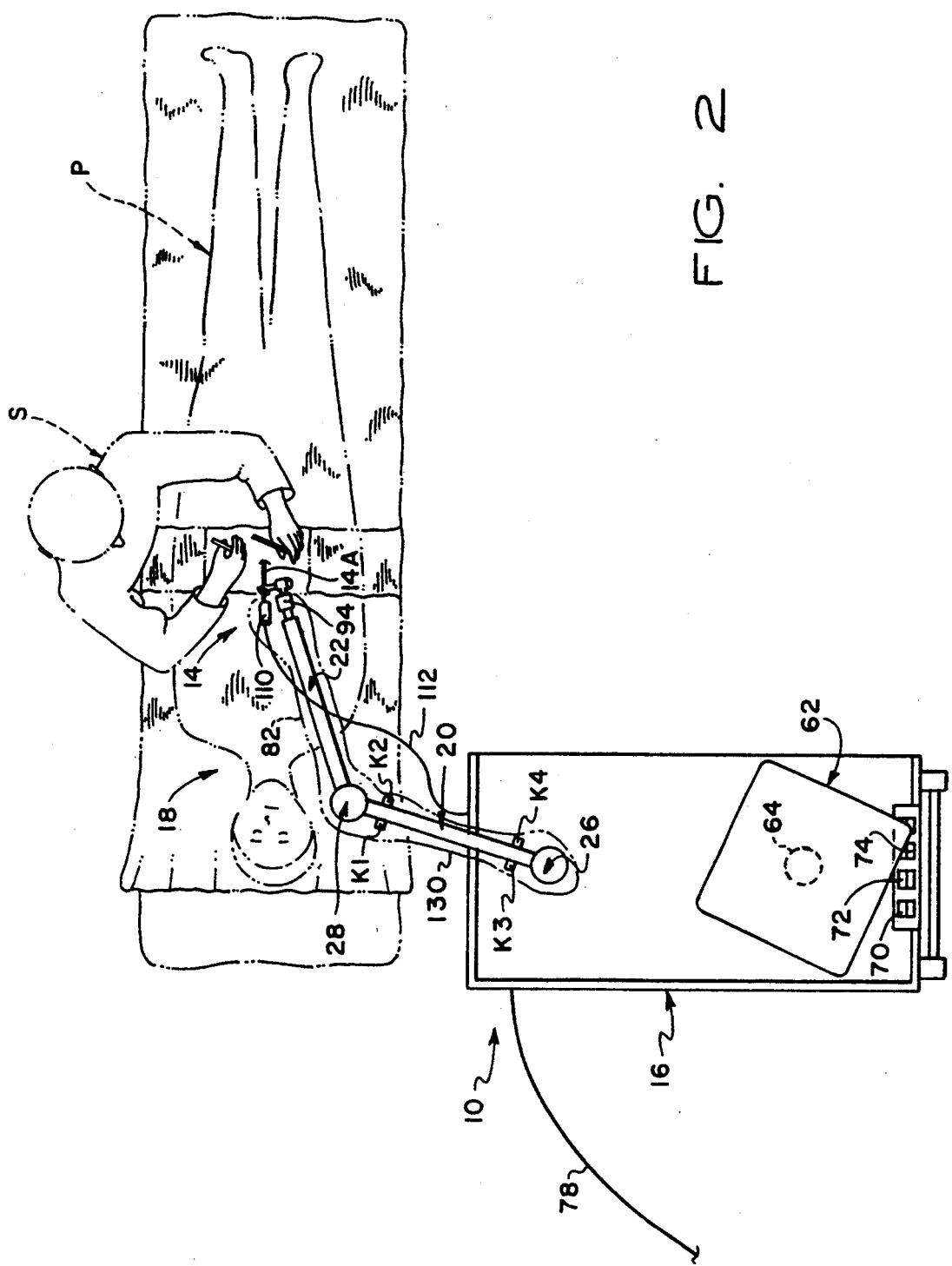
FIG. 2 is a top plan view of the portable console positioning apparatus and the surgical operating table depicted in FIG. 1.

Referring now to FIGS. 1 and 2, the surgical instrument support apparatus 10 is shown set up adjacent to an operating table 12 for positioning an endoscope instrument 14 during a surgical procedure in the abdominal cavity of a patient P. Stable support is provided by a portable console 16 which is equipped with lockable wheels W for permitting rolling movement of the console 16 from one station to another. The portable console 16 is parked adjacent to the operating table 12, and is positioned substantially at a right angle with respect to the operating table 12 to provide standing room for attendants who assist the surgeon S. After the portable console 16 has been positioned correctly, its wheels W are locked by depressing the wheel lock arms L, and the surgical instrument support apparatus 10 is made ready by an attendant.

The endoscope instrument 14 is supported by an articulated arm assembly 18 which includes a first support section 20 and a second support section 22, rotatably supported by an upright support shaft 24. The support shaft 24 is movably mounted on the console 16 for extension and retraction in elevation. The first support section 20 is movably coupled to the upright support shaft 24 by a bearing assembly 26 which permits rotational movement of the first support section 20 relative to the support shaft 24. Likewise, the second support section 22 is rotatably coupled to the first support section 20 by a bearing assembly 28.

The angular position of the first support section 20 relative to the second support section 22 is selectively locked and released by a band brake assembly (not shown) which includes first and second friction bands fitted about a coupling sleeve and movable from a released, non-engaging position to a locked, brake position in response to retraction of the friction bands. The friction bands are selectively retracted by first and second lever arms respectively (not shown), which are mounted for pivotal movement about a pin. One end of the first lever arm is connected to the free end of the first friction band, and the opposite end of the first lever arm is attached to the plunger of an electrical solenoid K1.

According to this arrangement, when the solenoid K1 is energized, the plunger retracts and draws the first lever arm in a clockwise movement. As this occurs, a coil spring is compressed, thereby releasing the first friction band from engagement against the coupling sleeve. When operating power is removed from the solenoid K1, the coil spring pushes the first lever arm end portion in counterclockwise movement, thereby drawing the first and second friction bands into engagement with the coupling sleeve, and locking the second support section 22 relative to the first support section 20. The second friction band is operated by a second solenoid K2 which is mounted on the opposite side of the support section 20, best seen in FIG. 2. The plunger of the second solenoid K2 is connected to the second lever arm and is mounted for pivotal movement on the pin. The solenoids K1 and K2 are electrically coupled in parallel to a source of electrical operating power through a position controller (not shown). It should be understood that many expedients are known for the position controller, the exact configuration not being necessary for the understanding of the present invention.

A bearing assembly 28 includes a cylindrical thrust bearing (not shown) which is connected to the first support section 20 by a bracket (not shown). The second support section 22 is attached to a cylindrical coupling sleeve (not shown) which receives the cylindrical thrust bearing in telescoping engagement. The first friction band is engageable against the coupling cylindrical coupling sleeve. The second friction band is fitted about the coupling sleeve and is actuated by the second solenoid K2. The thrust bearing is attached to the first support arm section 20 by a coupling sleeve, an annular collar, and the bracket.

Figure 3:
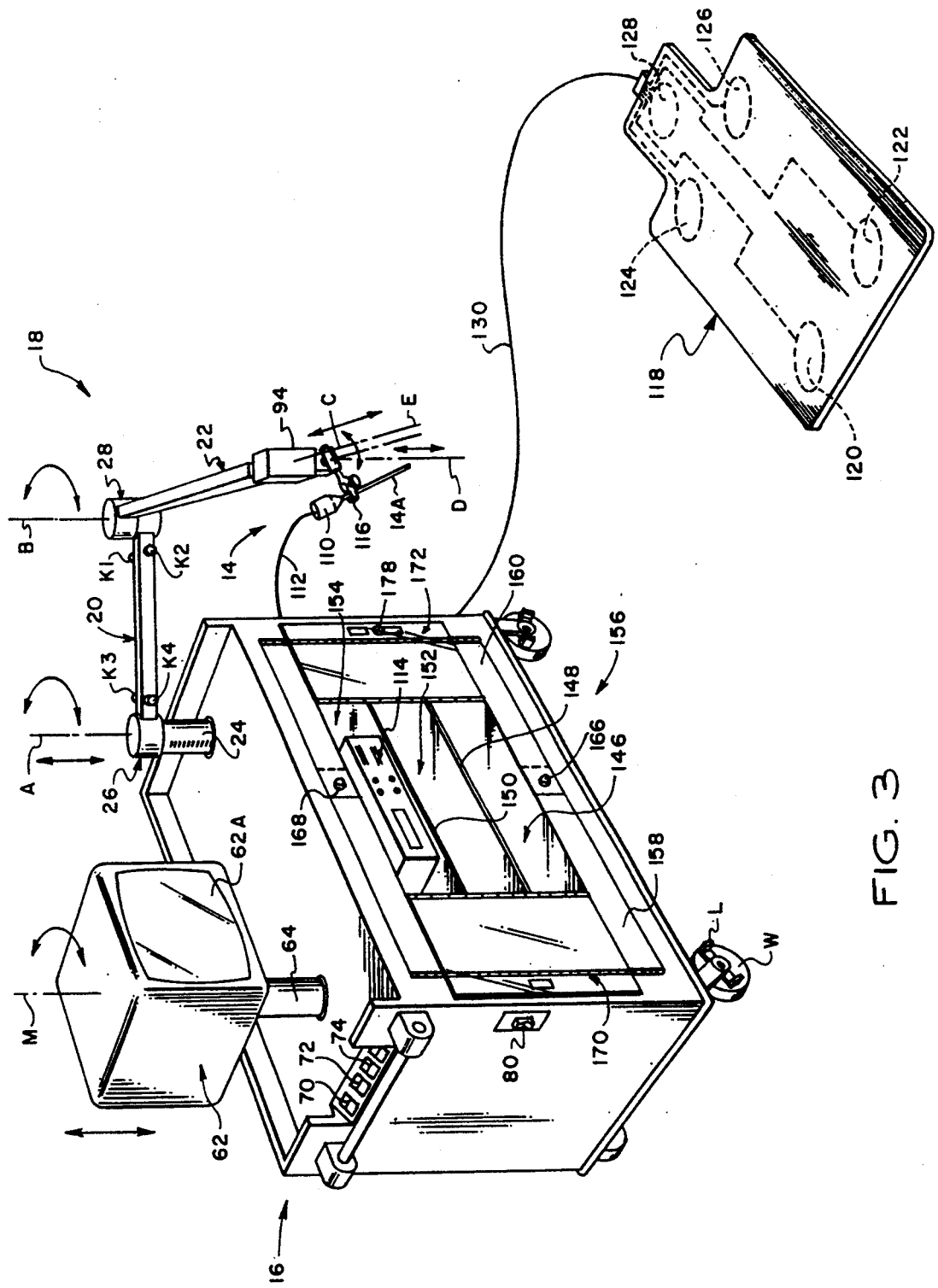
FIG. 3 is a perspective view of the portable console positioning apparatus of FIG. 1 with the surgical operating table removed.

As best seen in FIGS. 1–3, the first support section 20 is rotatably coupled to the upright support shaft 24 by a bearing assembly 26. The bearing assembly 26 has substantially the same construction as the bearing assembly 28, with the distal end of the upright support shaft 24 being engaged by a pair of friction bands (not shown) which are attached to lever arms and solenoids K3 and K4 respectively for selectively locking and releasing the angular position of the support section 20 with respect to the upright support shaft 24. The solenoids K3 and K4 are electrically wired in parallel with the solenoids K1 and K2 for receiving operating power through the position controller.

Figure 4:
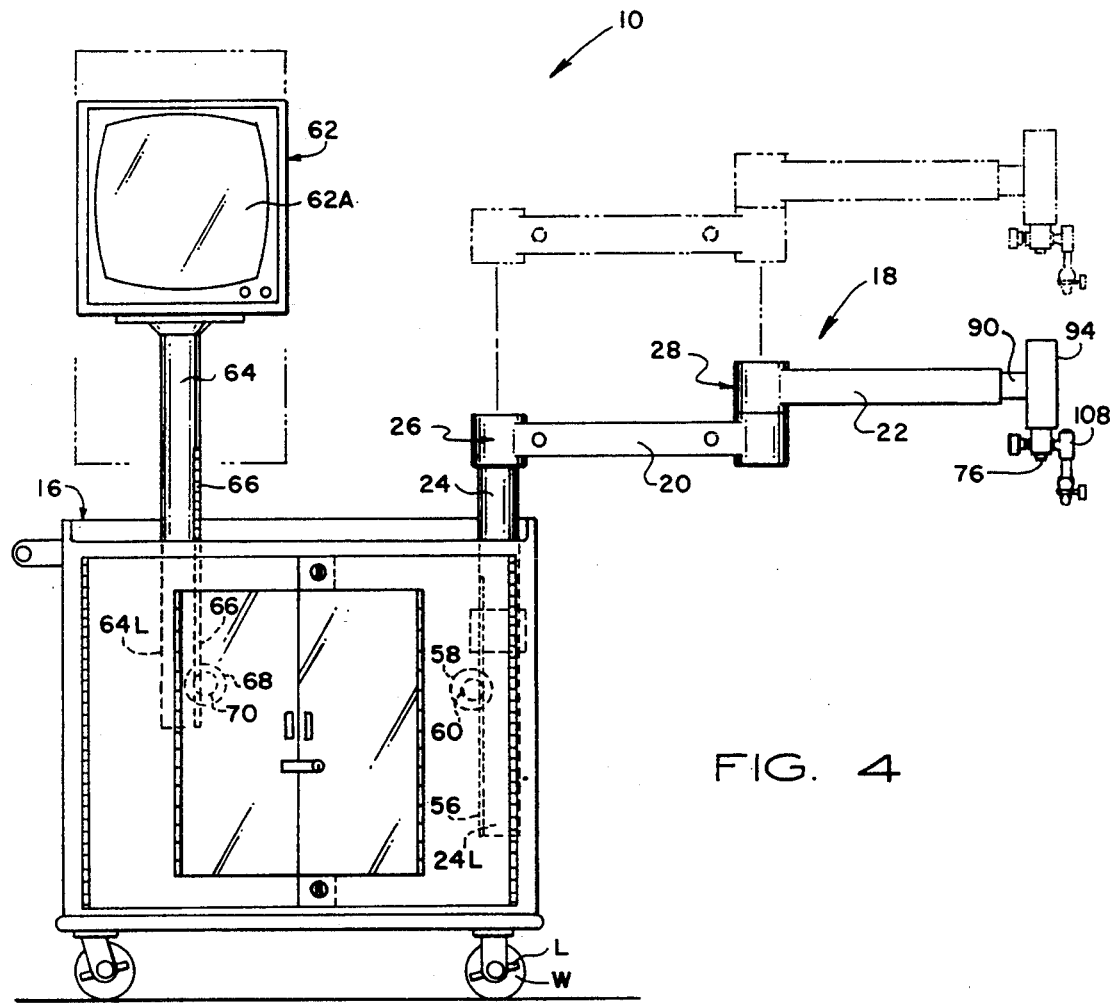
FIG. 4 is a front elevational view of the positioning apparatus of FIG. 1.

As depicted in FIG. 4, the upright support shaft 24 has a lower end portion 24L extending into the cabinet space of the console 16, and has a toothed rack 56 formed along its external surface. A drive motor 58 is coupled to the rack 56 by a pinion gear 60. The drive motor 58 is a reversible DC motor which is capable of driving the pinion gear 60 clockwise and counterclockwise, thereby extending and retracting the upright support shaft 24. When the drive motor 58 is de-energized, the pinion gear 60 holds the support shaft 24 at a fixed elevation.

In the preferred embodiment of the present invention, a video monitor 62 is supported on the console 16 by an upright shaft 64. The lower end 64L of the upright shaft 64 projects into the cabinet space of the console 16 and has a toothed rack 66 formed along its external surface. The video monitor 62 is lifted and lowered in elevation by a drive motor 68 which is coupled in driving relation with the rack 66 by a pinion gear 67. The video monitor 62 is pivotally attached to the upright shaft 64 so that its viewing screen 62A can be turned and aligned with the surgeon's field of view. The video monitor 62 is elevated above the articulated arm assembly 18 so that the surgeon's view will not be obscured.

Referring to FIGS. 3 and 4, elevation control of the video monitor 62 and coarse control of instrument elevation is provided by the drive motors 58 and 68 by actuation of switches 70 and 72, respectively, which are console mounted and operable by an attendant. The switches 70 and 72 are single-pole, double-throw switches and are operable in a momentary ON mode when depressed, and automatically turned OFF when released. Release and lock operation of the solenoids K1, K2, K3 and K4 is provided by a console mounted, single-pole, single-throw switch 74 which operates in the ON mode when depressed, and which automatically turns OFF when released. The solenoids K1, K2, K3 and K4 are also operable through a manual override switch 76 which is mounted on the articulated arm assembly 18 as discussed below.

When the console 16 is set up and locked in position as depicted in FIG. 1, an attendant connects the power service cable 78 to an AC power outlet and makes AC power available to the controller within the console unit by turning on the master switch 80. A DC power supply (not shown) within the controller provides the DC operating current for the drive motors and solenoids. The control switch 72 is then depressed to drive the articulated arm assembly 18 upwardly until an appropriate clearance elevation has been reached. The solenoids K1, K2, K3 and K4 are then released by depressing control switch 74 and the articulated sections 20 and 22 are manually extended over the operating table. After the approximate position has been established, the control switch 74 is released and the solenoids are de-energized, thereby locking the angular position of the sections 20 and 22. The video monitor 62 is elevated to an appropriate viewing elevation, and the viewing screen 62A is rotated in alignment with the surgeon's field of view. After the articulated arm is generally positioned, a sterile drape 82 may be installed to preserve the sterile environment.

Figure 5:
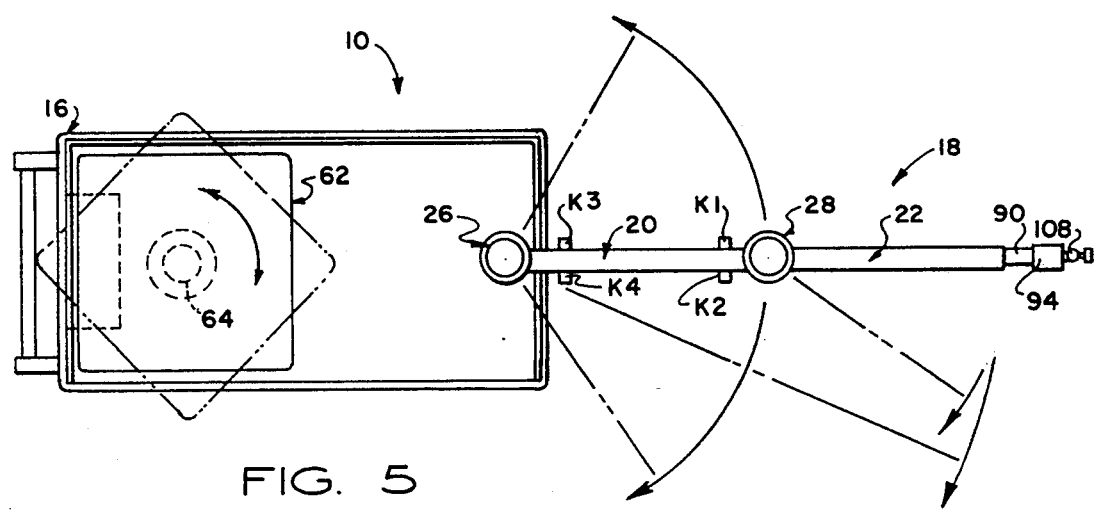
FIG. 5 is a top plan view thereof.

Referring to FIG. 5, fine adjustment along the longitudinal axis C is provided for the instrument position by a DC drive motor (not shown). The stator (not shown) of the DC drive motor is mounted in a fixed position on the support section 22 and has a rotor screw shaft (not shown) received in threaded engagement with a threaded coupling collar (not shown) which is attached to a tubular extension arm 90. The tubular extension arm 90 is received in telescoping engagement within the bore of the support section 22. Upon clockwise and counterclockwise rotation of the rotor screw shaft, the extension arm 90 is extended and retracted along the longitudinal axis C of the extension arm 90.

Fine adjustment of the instrument position along a vertical axis D is provided by a reversible DC drive motor (not shown). The drive motor is mounted within a tubular housing 94 which is oriented at a right angle with respect to the longitudinal axis C of the extension arm 90. The drive motor has a rotor screw shaft (not shown) which is received in threaded engagement with a coupling collar (not shown). The coupling collar is secured to the end of a tubular extension arm 100 which is slidably received in telescoping engagement within the bore of the tubular housing 94. Upon clockwise and counterclockwise rotation of the threaded rotor shaft, the extension arm 100 is lifted and lowered in elevation along the vertical axis D of the extension arm 100.

As best seen in FIG. 3, the endoscope instrument 14 is a fiber optic endoscope which has an insertion probe 14A and a fiber optic video camera 110. The fiber optic video camera 110 is connected by a signal cable 112 to a video recorder unit 114 inside the cabinet space of the console 16. A light source is incorporated in the probe section 14A of the endoscope, whereby an image of the internal cavity is provided on the viewing screen 62A. According to this arrangement, the surgeon observes the video presentation and makes fine adjustments of the fiber optic camera orientation by selectively actuating the drive motors, after the initial insertion orientation has been established. Selective actuation of the reversible drive motors is provided by a pressure responsive foot switch assembly 118. The foot switch assembly 118 includes longitudinal extend and retract foot switches 120 and 122 and up and down pressure responsive foot switches 124 and 126. A master control foot switch 128 is also provided.

The foot switches 120, 122, 124 and 126 are momentary ON switches which automatically turn OFF in the absence of pressure. The master control foot switch 128 is a single-pole, single-throw momentary ON switch which is electrically coupled to an enable circuit within the position controller. The enable circuit locks up four control relay switches which are coupled in series with the foot switches 120, 122, 124 and 126. Actuation of the master control foot switch 128 sets the enable circuit, thereby rendering each foot switch active. A second actuation of the foot switch causes the enable circuit to reset, thereby automatically disabling each of the foot switches 120, 122, 124 and 126.

If fine adjustment of elevation or longitudinal position is desired during the course of a surgical procedure, the operating surgeon S applies momentary foot pressure to the master control foot switch 128 which enables the foot switches 120, 122, 124 and 126. The surgeon S then applies foot pressure to the appropriate switch until the desired video presentation is obtained. After the desired video presentation is obtained, momentary foot pressure is again applied to the enable foot switch 128 which disables the fine control switches and prevents inadvertent adjustment.

The foot switches 120, 122, 124 and 126 and the master control foot switch 128 are electrically coupled to the position controller by a multiple conductor cable 130. The position controller applies DC operating voltage of the appropriate polarity to the drive motors in response to actuation of the foot switches 120, 122, 124 and 126.

The position controller also applies DC operating voltage of the appropriate polarity to the arm and monitor drive motors 58 and 68 respectively in response to actuation of the console mounted switches 70 and 72. The solenoids are energized and the band brakes are released by actuation of the console mounted arm control switch 74, or the manual override switch 76 mounted on the articulated arm. The manual override switch 76 which is attached to the underside of the extension arm 100 permits an attendant standing at the end of the console 16 to exercise coarse position control of monitor elevation and articulated arm elevation during initial setup. It also permits the surgeon S to exercise coarse position control of the articulated arm, and hands free, fine control of instrument elevation and extension by applying foot pressure to selected foot switches 120, 122, 124, 126 and 128.

The console 16 is positioned on one side of the operating table, and the foot switch assembly 118 is positioned on the opposite side, adjacent to the operating table support pedestal 144. This orientation of the console 16 provides access to the surgical site for an attendant, without blocking the surgeon's view of the viewing screen 62A. The switches 120, 122, 124, 126 and 128 are know and referred to in the art as "pancake" switches, and are sandwiched between two sheets of flexible rubber material. The multiple conductor cable 130 is coupled to the position controller by a multiple pin connector which can be plugged in and disconnected as desired.

Consequently, the foot switch assembly 118 can be folded or rolled up and stored within the lower storage space 146 within the console 16. The storage space of the console 16 is partitioned by two divider panels 148, 150 providing separate storage compartments 152, 154. As shown in FIG. 3, the video recorder unit 114 is received within the upper storage compartment 154, and is supported by the upper divider panel 150. The next lower storage compartment 152 is adapted for storage of accessories such as a video camera, endoscope equipment and video interconnect equipment. The lower storage space 146 is adapted to receive the electrical power cable, the foot switch assembly 118 and the foot switch conductor cable 130.

The storage compartments are secured by a dual door assembly 156. The dual door assembly 156 includes first and second metal panels 158 and 160 which are connected by hinges 162 and 164 to the front frame of the console 16. The panels 158 and 160 have overlapping end portions which are secured together by quarter turn screw fasteners 166 and 168.

The contents of the storage compartments are made visible through double glass doors 170 and 172. The glass doors 170 and 172 are received within rectangular cutout windows within the metal doors 158 and 160. The glass doors 170 and 172 are mounted on the metal doors by hinges 174 and 176. The glass doors are secured together by a key lock 178. In addition to revealing the equipment stored within the internal console compartments, the glass doors also permit wireless communication, for example, FM or infrared signalling, between a hand-held controller and the video recorder unit 114 when the glass doors are closed. The primary purpose of the double glass doors 170 and 172 is to permit quick and easy access to the accessories which are stored within the internal compartments of the console 16. The larger metal doors 158 and 160 are opened only when it is necessary to perform maintenance or repairs.

In addition to providing a stable platform for the endoscope instrument 14, the console 16 provides stable support for the video monitor 62. The video monitor 62 is mounted for rotation on the upright shaft 64, and is rotatable clockwise and counterclockwise with respect to the longitudinal axis M for alignment with the field of view of the operating surgeon S. The video monitor 62 is electrically connected to the video recorder unit 114 for providing a real time display of the internal images produced by the video camera 110. Additional viewing monitors may be coupled to the video monitor 62 and to the video recorder unit 114 for observation by attendants.

Fine positioning control of the endoscope instrument 14 may be accomplished quickly and easily by actuating the appropriate switches on the foot switch assembly 118. The articulated arm 18 can be readjusted as desired by the surgeon by actuating the manual override switch 76. Otherwise, the positioning control is carried out entirely by foot movements, thereby freeing the surgeon's hands for manipulating other surgical instruments, for example, a grasper, hook, spatula, forceps and dissector, as indicated in FIG. 1.

Because the arm assembly 18 is articulated, it permits the console 16 to be set up away from the operating table, out of the sterile field. Because of the stable support provided by the console 16, no additional support equipment is required. The surgical instrument support apparatus 10 is easy to set up by one person and requires only minimal training. No additional support personnel are required for holding or stabilizing the endoscope instrument 14. Because of the range of the articulated arm assembly 18, the console 16 can be oriented away from the operating table, thereby providing access to the surgical site on the near side of the operating table. The sterile drape 82 completely covers the articulated arm and permits the surgeon S to operate freely without contaminating the sterile field. The manual override switch 76 is covered by the sterile drape 82 and is actuated by finger pressure applied through the drape.

Figure 6:
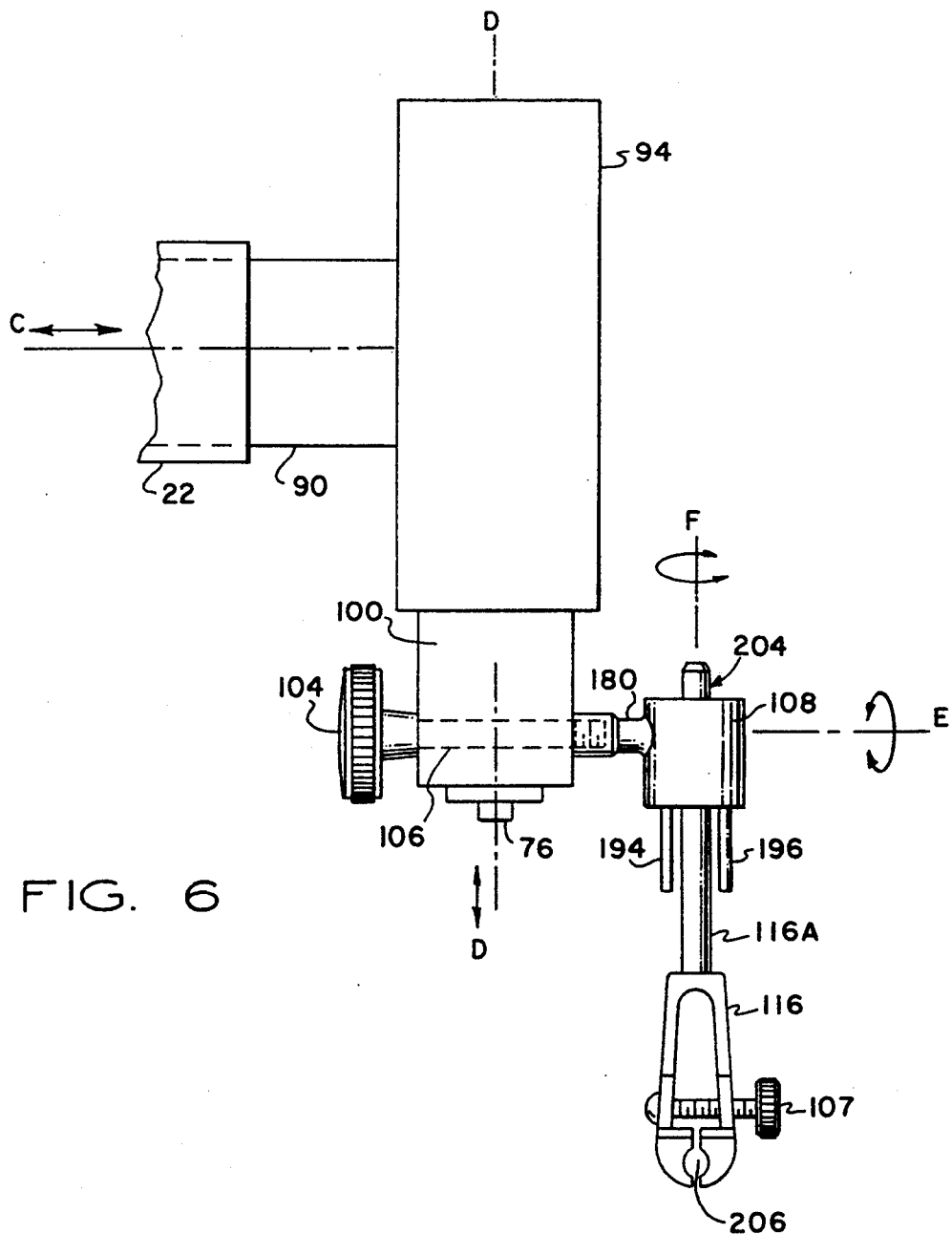
FIG. 6 is a broken away front view of an arm assembly employing a quick-disconnect clamp practiced in accordance with the principles of the present invention.

Referring to FIGS. 5-11, the endoscope instrument 14 is secured to a rotatable collar 108 extending from the extension arm 100. The collar 108 is secured for rotation on the distal end of the extension arm 100 by a screw clamp 104. The screw clamp 104 includes a threaded shaft 106 for engaging a threaded portion 180 formed on the outside wall of the collar 108. In an untightened position, the screw clamp 104 permits free rotation of the collar 108 about the longitudinal axis E. The screw clamp 104 can then be tightened to maintain the collar 108 at a preferred angle. As best seen in FIGS. 6 and 8, the collar 108 includes a bore 182 extending therethrough from top to bottom along the axis F which is substantially perpendicular to the longitudinal axis E. The bore 182 is countersunk or counterbored, preferably about three-quarters along its length from the bottom, to form an inner sidewall 184. The inner sidewall 184 is further defined by an annular groove 186 for engagement with a quick release bayonet connector 188 described hereinbelow. A portion of the bore 182 which is not counterbored acts as a pilot guide 190 for guiding the distal end 204 of the shaft 116A through the collar 108 as described in more detail hereinbelow. The distal end 204 of the shaft 116A is preferably tapered so that insertion into the pilot guide is aided.

Figure 7:
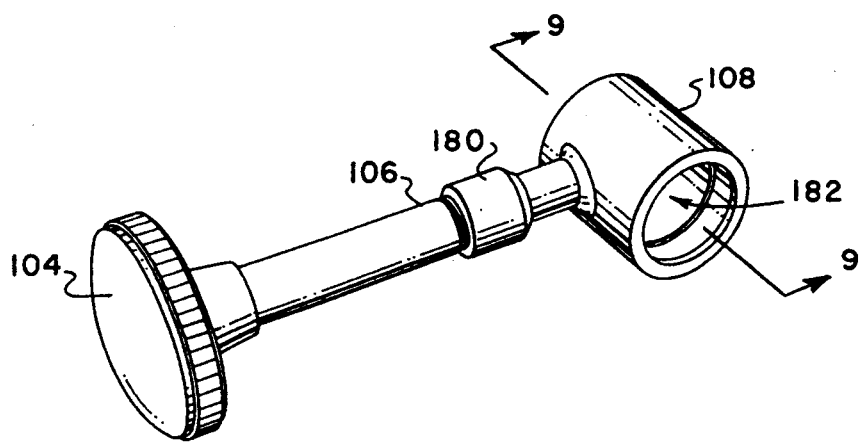
FIG. 7 is a perspective view of an adjustable collar depicted in FIG. 6.
Figure 12:
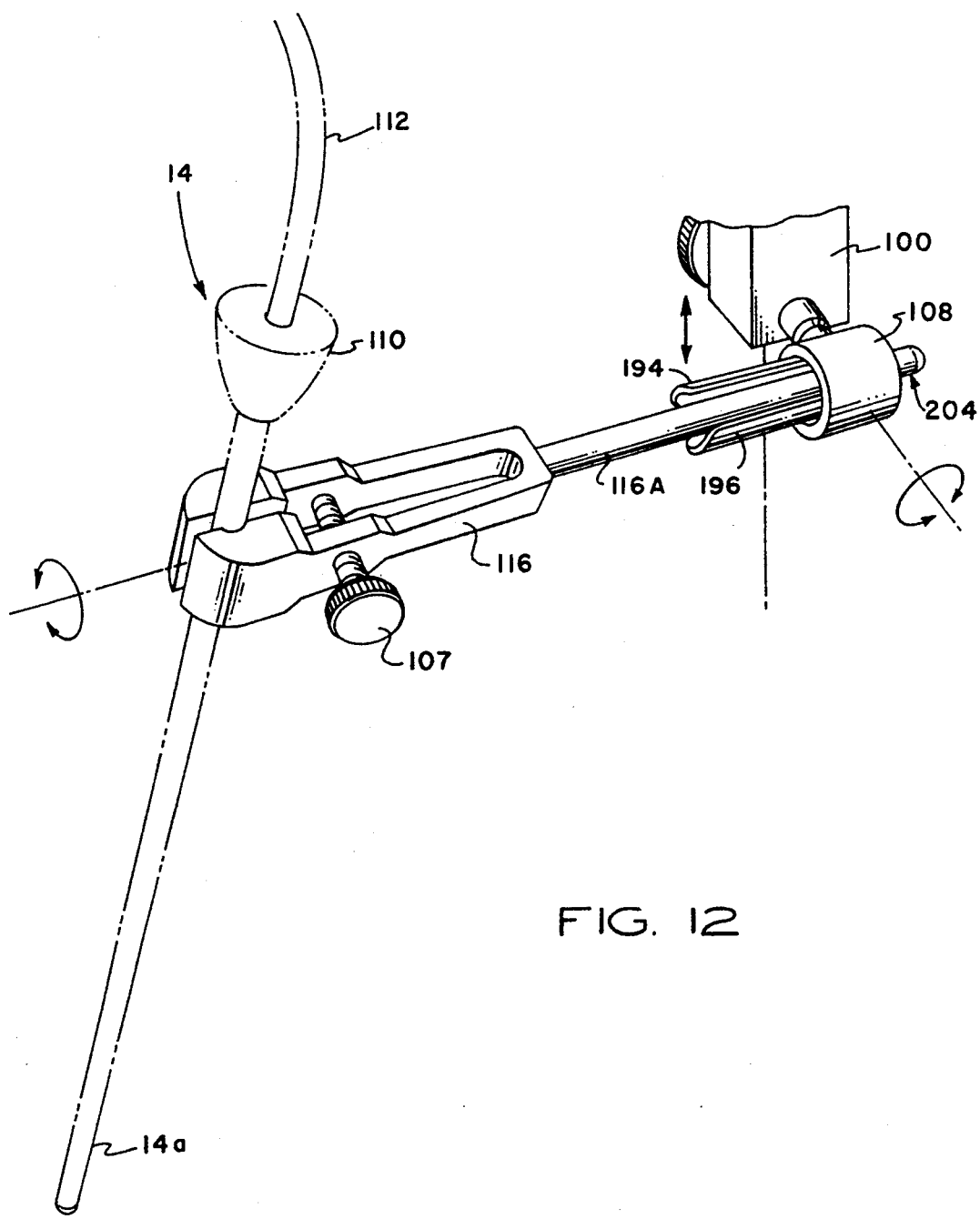
FIG. 12 is a perspective view of an endoscope instrument installed in the quick-disconnect clamp of the present invention.

As shown in FIG. 7, attached to the shaft 116A is a quick release bayonet connector 188. The bayonet connector 188 is formed by an annular shoulder 192 having first and second springable arms 194 and 196 extending therefrom. The annular shoulder 192 is fitted about the shaft 116A with the first and second springable arms 194 and 196 extending downwardly along the shaft 116A towards the clamp 116 and flaring outwardly. The outer surface of the arms 194 and 196 have formed thereon, a rib or boss 198 in the general shape of an arc segment. Preferably, the boss 198 is chamfered on its top edge 200 to aid the bayonet connector 188 as it is inserted into the counterbore formed by the inner sidewall 184. The boss 198 has a bottom edge 202 for engaging and interlocking within the annular groove 186, as shown in FIG. 9.

The sterile clamp 116 preferably made of a disposable engineered resin, for example 25% glass-filled nylon or "KEVLAR" film polyester, or a reusable metallic material such as titanium or stainless steel. The clamp 116 is inserted through a preformed opening in the sterile drape 82 (FIGS. 1 and 2). The clamp 116 has an aperture 206 (FIG. 9) adjustable by screw clamp 107 for accommodating a wide range of endoscope sizes/diameters. The clamp 116 is coupled to the collar 118 by compressing the springable arms 194 and 196 and inserting the shaft 116A through the bottom of the collar 108 and into the bore 182. Compression of the springable arms 194 and 196 permits each boss 198 to fit within the inner sidewall 184. With the shaft 116A inserted and the arms 194 and 196 compressed, the clamp 116 may be freely rotated about the axis F. Once within the sidewall 184, the springable arms 194 and 196 may be released allowing them to expand and for each boss 198 to engage the annular groove 186 formed therein. It is to be understood that while the preferred embodiment employs two arms 194 and 196, three or more arms may be used without departing from the scope of the present invention.

In the inserted position, the distal end 204 of the shaft 116A extends through the top wall of the collar 108. The extension of the distal end 204 permits the surgeon S to apply a downward force in conjunction with an applied compressive force to the arms 194 and 196, to aid in withdrawing the clamp 116 from the collar 108. Preferably, the insert length (i.e. the distance from the distal end 204 of shaft 116A to the top of the inner sidewall 184) is equal or greater than the pilot length (i.e. the total length of the inner sidewall 184).

Upon completion of a surgical procedure, the clamp 116 is removed by compressing the springable arms 194 and 196 which are covered by the sterile drape 82, the articulated arm assembly 18 is retracted, released and folded inwardly, and the video monitor 62 is retracted. The accessories, including the foot switch assembly 118 and signal conductor cable 130, are stored within the console compartments, and the glass doors 170, 172 are locked. The portable console assembly 10 is then ready for storage out of the operating area, and may be moved from one operating room to another.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

I claim:

1. A surgical instrument holder comprising:

a coupling collar having a bore extending therethrough and a counterbore defining an inner wall with an annular groove formed therein;

a shaft having an end portion which is insertable through the bore;

quick disconnect means disposed on the shaft end portion for releasably coupling the shaft to the coupling collar by engaging the annular groove formed within the inner wall, the quick disconnect means being compressible and expandable for lockably engaging the coupling collar as the shaft is inserted into the bore, and being disengageable from the coupling collar by applying a compressive force to the disconnect means as the shaft is withdrawn from the bore; and, clamp means disposed on the shaft for clamping a surgical instrument.

2. A surgical instrument holder as recited in claim 1 wherein the quick disconnect means includes two resilient arms, each arm having a radially projecting boss engageable with the annular groove, the arms being compressible for inserting the shaft into the bore and expandable for lockably coupling the shaft to the coupling collar upon release thereof.

3. A surgical instrument holder as recited in claim 2 wherein each boss is chamfered in a direction to aid insertion of the quick disconnect means into the counterbore.

4. A surgical instrument holder as recited in claim 2 wherein each boss is chamfered in a direction to aid withdrawal of the quick disconnect means out of the counterbore.

5. A surgical instrument holder as recited in claim 1 wherein the clamp means is made of a stainless steel material.

6. A surgical instrument holder as recited in claim 1 wherein the clamp means is made of a nylon material.

7. A surgical instrument holding apparatus comprising:

a coupling collar defined by a cylindrical body intersected by a bore and a counterbore, the counterbore forming an inner wall and defining a guide surface through the body to a position less than the total length of the cylindrical body, the inner wall having an annular groove formed therein;

a shaft having an end portion which is insertable through the bore of said collar;

a quick release bayonet connector disposed on the shaft and insertable into the counterbore for lockable engagement with the annular groove, the bayonet connector being releasable in response to an applied compressive force; and a clamp coupled to the shaft for holding a surgical instrument, the clamp being adjustable for accommodating different surgical instrument sizes.

8. A surgical instrument holding apparatus as recited in claim 7 wherein the quick release bayonet connector comprises an annular shoulder and a pair of spring arms depending therefrom in radially spaced relation to the shaft and accessible outside the coupling collar, each arm including an external rib for engaging the annular groove in the inner wall and being releasable in response to applying a compressive force to the arms.

9. A surgical instrument holding apparatus as recited in claim 7 wherein a portion of the bore disposed above the counterbore provides a guide for centering the shaft therein.

10. A surgical instrument holding apparatus as recited in claim 7 wherein the end portion of the shaft is tapered for engagement with the guide surface.

11. An assembly for selectively positioning and releasably holding a surgical instrument comprising, in combination:

a portable console:

an articulated support arm movably mounted in elevation relative to the console, the articulated support arm having a proximal support arm section and a distal support arm section;

a coupling collar having a retentive cavity coupled to the distal support arm section of the articulated support arm; and, a clamp assembly for holding a surgical instrument, the clamp assembly including a shaft and quick disconnect means disposed thereon for lockable engagement with the retentive cavity in the coupling collar, the clamp assembly being releasable in response to applying a compressive force to the quick disconnect means.

12. An assembly as recited in claim 11 wherein the retentive cavity extends through the coupling collar and a portion of the shaft projects out of the coupling collar.

13. An assembly as recited in claim 11 wherein the quick disconnect means includes an annular shoulder and a pair of resilient arms disposed about the shaft and flaring outwardly about the shaft, the arms being radially deflectable as the shaft is inserted into the retentive cavity.

14. An assembly as recited in claim 13 wherein each arm further includes a boss disposed on its outer surface for engaging an annulus groove within the retentive cavity.

15. An assembly as recited in claim 14 wherein each boss is chamfered in a direction to aid insertion of the quick disconnect means into the retentive cavity.

16. An assembly as recited in claim 14 wherein each boss is chamfered in a direction to aid withdrawal of the quick disconnect means out of the retentive cavity.

* * * * *